(12) United States Patent
Yu et al.

(10) Patent No.: US 7,556,427 B2
(45) Date of Patent: Jul. 7, 2009

(54) X-RAY RADIOGRAPHY APPARATUS AND X-RAY GENERATOR MOVING DEVICE

(75) Inventors: Aimin Yu, Beijing (CN); Xiumin Liu, Beijing (CN); Jia Chen, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/059,564

(22) Filed: Mar. 31, 2008

(65) Prior Publication Data

US 2008/0240362 A1 Oct. 2, 2008

(30) Foreign Application Priority Data

Apr. 2, 2007 (CN) .......................... 2007 1 0092143

(51) Int. Cl.
*H05G 1/02* (2006.01)
(52) U.S. Cl. ........................................ 378/196; 378/197
(58) Field of Classification Search .......... 378/193–198
See application file for complete search history.

(56) References Cited

U.S. PATENT DOCUMENTS

| | | | | |
|---|---|---|---|---|
| 2,491,224 A | * | 12/1949 | Stava | 378/26 |
| 2,588,124 A | * | 3/1952 | Kizaur | 378/177 |
| 2,668,912 A | * | 2/1954 | Goldfield et al. | 378/190 |
| 4,435,830 A | | 3/1984 | Suzuki et al. | |
| 4,541,293 A | | 9/1985 | Caugant et al. | |
| 4,894,855 A | | 1/1990 | Kresse | |
| 5,081,661 A | * | 1/1992 | Larsson | 378/197 |
| 5,661,772 A | | 8/1997 | Bar et al. | |
| 6,155,713 A | | 12/2000 | Watanabe | |
| 6,169,780 B1 | | 1/2001 | Yoshimura et al. | |
| 6,325,537 B1 | | 12/2001 | Watanabe | |
| 6,609,826 B1 | | 8/2003 | Fujii et al. | |
| 6,851,853 B2 | | 2/2005 | Nakagawa et al. | |
| 7,018,097 B2 | | 3/2006 | Schmitt | |

\* cited by examiner

*Primary Examiner*—Hoon Song
(74) *Attorney, Agent, or Firm*—Armstrong Teasdale LLP

(57) ABSTRACT

The present invention provides an X-ray radiography apparatus constructed so as to be capable of moving an X-ray generator to as low a position as possible. A X-ray radiography apparatus is of the X-ray radiography apparatus that includes a table which has a transverse direction and a longitudinal direction, and which includes a first X-ray detector and is capable of placing a subject thereon, an X-ray generator that applies X rays to the subject placed on the table, and an X-ray generator moving device that moves the X-ray generator in the longitudinal direction of the table and upward and downward directions thereof. The X-ray generator moving device includes a guide rail disposed in the longitudinal direction in the neighborhood of the table, a guide support post that guides the X-ray generator movably up and down, and a moving member which is formed in an L shape extending in a transverse direction and extending in a longitudinal direction and which is coupled to the guide rail and the guide support post and moved along the guide rail.

18 Claims, 7 Drawing Sheets

X-RAY RADIOGRAPHY APPARATUS AND X-RAY GENERATOR MOVING DEVICE

CROSS REFERENCE TO RELATED APPLICATIONS

This application claims the benefit of Chinese Patent Application No. 200710092143.X filed Apr. 2, 2007, which is hereby incorporated by reference in its entirety.

BACKGROUND OF THE INVENTION

The subject matter disclosed herein relates to a radiation radiography apparatus (a radiation CR (Computed Radiography) apparatus), and specifically to an X-ray radiography apparatus capable of moving an X-ray tube.

Upon diagnosis of a subject, an X-ray penetrated image of the subject is photographed or imaged depending on the state of a disease or injury of the subject while the subject remains standing. Alternatively, its X-ray penetrated image is photographed while the subject lies down on a table. Therefore, there is provided an X-ray radiography apparatus wherein in order to enable the radiography of the subject while the stand remains standing, a stand is provided with an X-ray detector and a table is provided with an X-ray detector. Even in the case of the X-ray detector of the stand and the X-ray detector of the table, an X-ray generator needs to apply an X-ray beam even to any region of the subject.

FIG. 7 shows a conventional X-ray radiography apparatus 200. The X-ray radiography apparatus 200 is equipped with a table 231 provided with an X-ray detector 234-1, and a stand 232 provided with an X-ray detector 234-2. An X-ray generator 210 including X-ray tube is placed on a movable guide support post 241. The guide support post 241 is movable on rails disposed along the side surface of the table 231. Thus, the X-ray generator 210 can apply an X-ray beam even to any region of a subject lying down on the table 231. The stand 232 is disposed in the neighborhood of the table 231. The X-ray generator 210 can apply an X-ray beam even to the X-ray detector 234-1 of the stand 232.

However, the X-ray generator 210 supported by the guide support post 241 can only photograph a region at a height of about 550 mm or more even when it is moved to the lowest position. When, for example, regions located below the knees of the subject are photographed or imaged in a state in which the subject is standing, it can photograph the same only when the subject lies down on the table 231. Under such circumstances, there are cases in which it takes time to conduct a diagnosis and the subject suffers pain.

Therefore, it is desirable is to provide an X-ray radiography apparatus constructed so as to be capable of moving an X-ray generator to as low a position as possible.

SUMMARY OF THE INVENTION

A X-ray radiography apparatus of the present invention aims to provide an X-ray radiography apparatus capable of lowering an X-ray generator to a position as close as possible to a floor.

In a first aspect, an X-ray radiography apparatus of the present invention comprises a table having a transverse direction and a longitudinal direction, which is provided with a first X-ray detector and capable of placing a subject thereon, an X-ray generator for applying X rays to the subject placed on the table, and an X-ray generator moving device for moving the X-ray generator in the longitudinal direction of the table and upward and downward directions thereof. And the X-ray generator moving device includes a guide rail disposed in the longitudinal direction in the neighborhood of the table, a guide support post that guides the X-ray generator movably up and down, and a moving member which is formed in an L shape extending in a transverse direction and extending in a longitudinal direction and which is coupled to the guide rail and the guide support post and moved along the guide rail.

In the X-ray radiography apparatus according to the first aspect, the moving member is shaped in the L-shaped fashion. The guide support post for guiding the X-ray generator movably up and down is coupled to the moving member. Therefore, the X-ray generator can be lowered to near the floor without causing interference with the guide rail. It is thus possible to photograph the regions below the knees of the subject even in the standing state of the subject.

In the X-ray radiography apparatus according to a second aspect, when it is desired to move the moving member to an edge portion of the guide rail, the guide support post is placed outside as viewed in a longitudinal direction thereof from the edge portion of the guide rail.

In the X-ray radiography apparatus according to the second aspect, the guide support post is placed outside as viewed in the longitudinal direction from the edge portion of the guide rail. Therefore, there is a need to provide space in the longitudinal direction. However, even though broad space is not so required, the X-ray generator can be lowered to near the floor without interfering in the guide rail.

The X-ray radiography apparatus according to a third aspect further includes a stand having a second X-ray detector and disposed adjacent to the subject.

The X-ray radiography apparatus according to the third aspect is provided with the stand that enables radiography while the subject remains standing, together with the table on which the subject lies down. Thus, an operator is able to freely diagnose imaging regions according to diagnosed regions of the subject.

In the X-ray radiography apparatus according to a fourth aspect, the X-ray generator moving device has a carrier included in the guide support post, which moves the X-ray generator in the transverse direction.

In the X-ray radiography apparatus according to the fourth aspect, the X-ray generator can be moved not only in the longitudinal, upward and downward directions but also in the transverse direction. Therefore, the operator is able to freely move the X-ray generator to a region of the subject that needs its diagnosis.

In the X-ray radiography apparatus according to a fifth aspect, the moving member has a sliding member that slides in contact with a floor.

The moving member is of the L shape that extends in the transverse direction and extends in the longitudinal direction and is not placed on the guide rail. Thus, if the self weight of the moving member is not supported, then bending moment is applied to the guide rail, so that the guide rail becomes easy to fail. Therefore, if the moving member is provided with the sliding member, then its own weight can be supported by the sliding member. Thus, no bending moment is applied to the guide rail. Since the sliding member slides with the moving member, no problem occurs upon traveling of the moving member. Particularly when the moving member supports the weight of the guide support post as well as being coupled to the guide support post, the effect of the sliding member is large.

In the X-ray radiography apparatus according to a sixth aspect, the guide support post has a sliding member that slides in contact with a floor.

Since the guide support post is provided with the X-ray generator, its own weight is large and bending moment is applied even to the guide support post per se. If the self weight of the guide support post is not supported, then bending moment is applied to the guide rail, so that the guide rail becomes easy to fail or break down. Therefore, if the guide support post has the sliding member, no bending moment is applied to the guide rail because the self weight of the guide support post can be supported by the sliding member. Since the sliding member slides with the guide support post, no problem occurs upon the traveling of the guide support post.

The X-ray radiography apparatus according to a seventh aspect is provided with a control device for controlling the traveling of the X-ray generator. When the moving member is placed in a first range as viewed in the longitudinal direction, the control device controls the X-ray generator in such a manner that the X-ray generator is moved up and down within a predetermined height range of the guide support post.

In the X-ray radiography apparatus according to the seventh aspect, the moving member is moved up and down within the predetermined height range of the guide support post when the moving member is placed in the first range as viewed in the longitudinal direction. If the first range extends from end to end as viewed in the longitudinal direction of the table, then the X-ray generator can be moved up and down within the range in which it does not collide with the table.

The X-ray radiography apparatus according to an eighth aspect is provided with a control device for controlling the traveling of the X-ray generator. When the X-ray generator is placed at a predetermined height or less, the control device controls the moving member in such a manner that the moving member is moved only within a second range.

In the X-ray radiography apparatus according to the eighth aspect, the moving member can be moved only within the second range when the X-ray generator is placed at the predetermined height or less. It is therefore possible to prevent the X-ray generator from accidentally colliding with the table or the like.

According to a X-ray radiography apparatus of the present invention, an X-ray generator can be moved to as low a position as possible, and the X-ray generator can be moved in a longitudinal direction of a table.

DETAILED DESCRIPTION OF THE INVENTION

Figure 1:
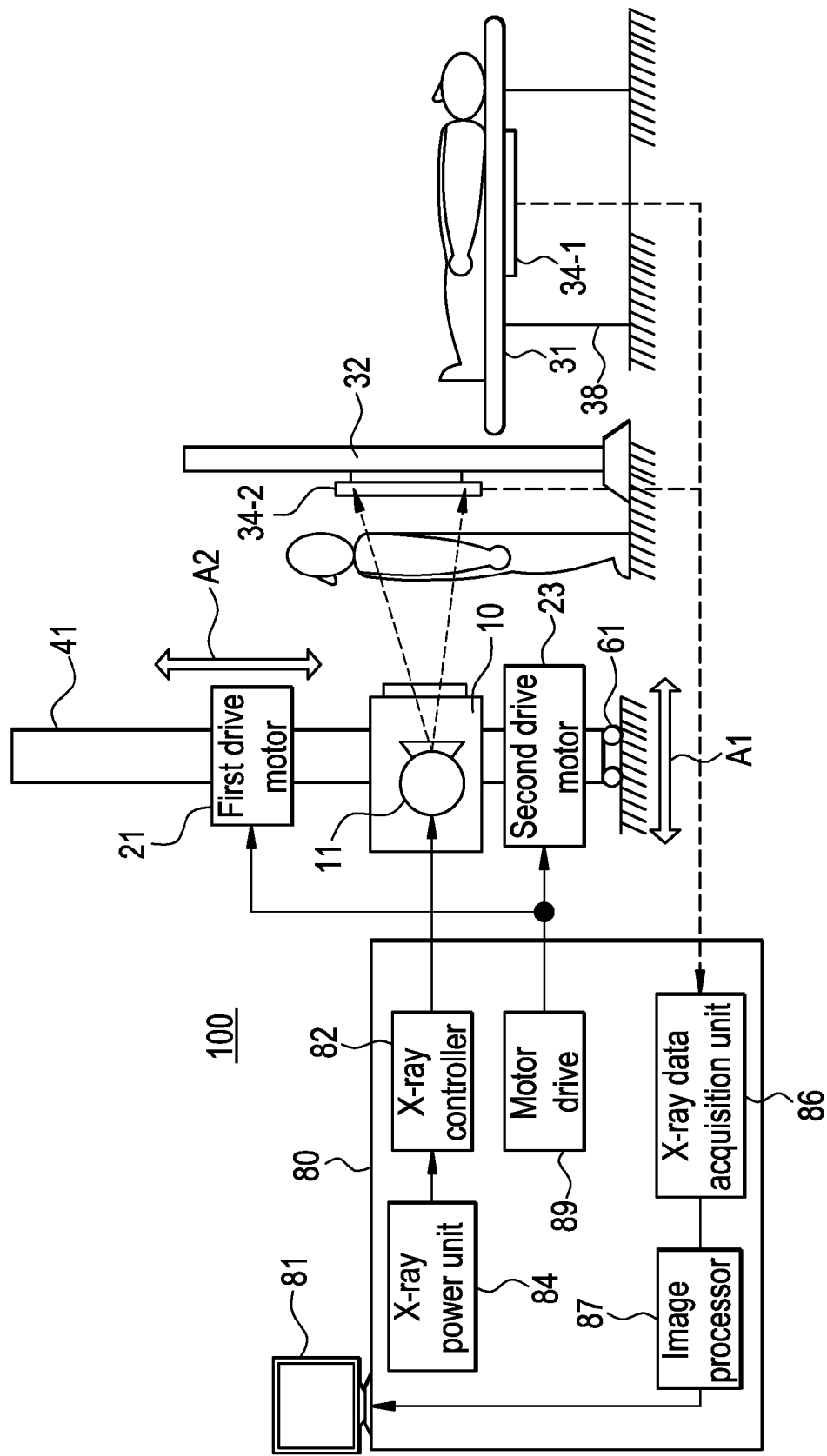
FIG. 1 is a block diagram showing a construction of an X-ray radiography apparatus 100 for obtaining an X-ray penetrated image of a subject.

FIG. 1 is a block diagram showing a construction of X-ray CR (Computed Radiography) apparatus 100 for obtaining an X-ray penetrated image of a subject. Classified broadly, the present X-ray CR apparatus has an X-ray tube unit 10 which radiates X rays, a table 31 on which the subject lies down, a stand 32 which X-ray photographs the subject in its standing state, and an operation console 80. The table 31 has a flat panel detector 34-1. The stand 32 has a flat panel detector 34-2. The flat panel detectors 34-1 and 34-2 are constituted of a scintillator, a light detector array, an X-ray exposure monitor, an electric substrate, etc. as principal constituent elements. The flat panel detector 34-2 mounted to the stand 32 is constructed so as to be movable up and down according to a photographed region of the subject. The flat panel detector 34-1 provided on the table 31 is constructed so as to be movable from side to side according to the photographed region of the subject, for example, the head or legs thereof. Incidentally, although the stand 32 is of a stationary type in FIG. 1, it may be constructed movably with tires added thereto.

The operation console 80 has an X-ray power unit 84, an image processor 87, a motor driver 89, etc. Image data transferred from the flat panel detector 34-1 or the flat panel detector 34-2 are sent to an X-ray data acquisition unit 86. The collected X-ray data are image-processed at the image processor 87. A display 81 displays an image-processed X-ray penetrated image thereon. There is no need to separately provide the flat panel detector 34-1 or the flat panel detector 34-2. One flat panel detector 34 may be constructed so as to be alternately interchanged by a flexible cable.

The X-ray tube unit 10 is held by the guide support post 41 and movable up and down in alignment with a diagnosed region of the subject as indicated by arrow A2. The X-ray power unit 84 and an X-ray controller 82 supply power of a suitable voltage current to an X-ray tube 11 of the X-ray tube unit 10. The X-ray tube unit 10 further includes an unillustrated collimator for designating an irradiated field of view of an X-ray beam. The X-ray beam radiated from the X-ray tube 11 is applied onto the subject via the collimator.

The guide support post 41 has a first drive motor 21 and a second drive motor 23. The guide support post 41 is constructed so as to be moved by bearings 61 each corresponding to a sliding member, etc. as indicated by arrow A1. The first drive motor 21 is a motor for moving the X-ray tube unit 10 to a suitable height of the guide support post 41 and is controlled by a motor driver 89 lying within the operation console 80. The second drive motor 23 is a motor for moving the guide support post 41 to a suitable position along the floor and is controlled by the motor driver 89 lying within the operation console 80. It is not necessary to move the X-ray tube unit 10 or the guide support post 41 by electromotion. The X-ray tube unit 10 or the guide support post 41 may be constructed so as to be movable manually.

Figure 2:
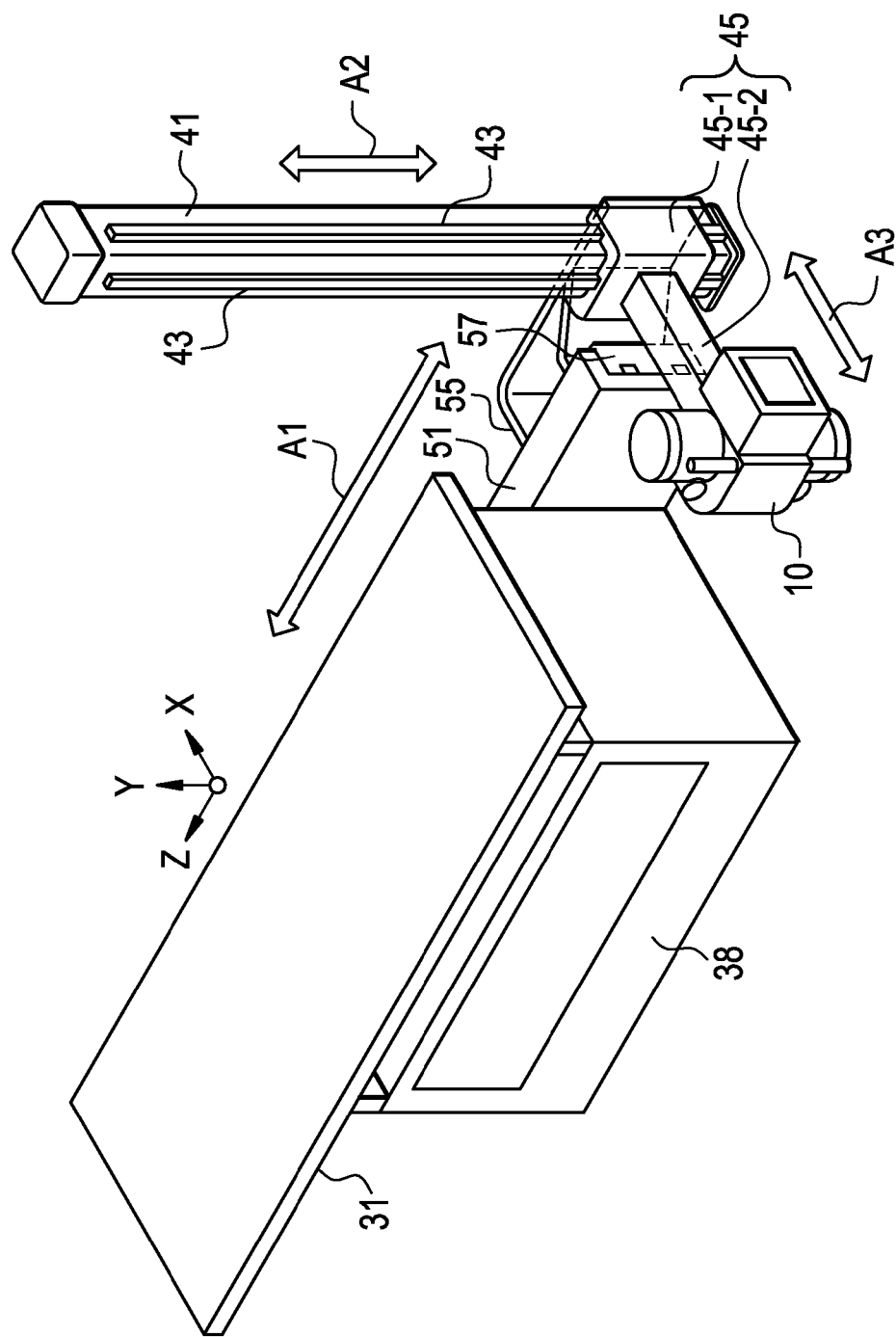
FIG. 2 is a front perspective view showing constructions of a table 31 and a guide support post 41 employed in an embodiment.
Figure 3:
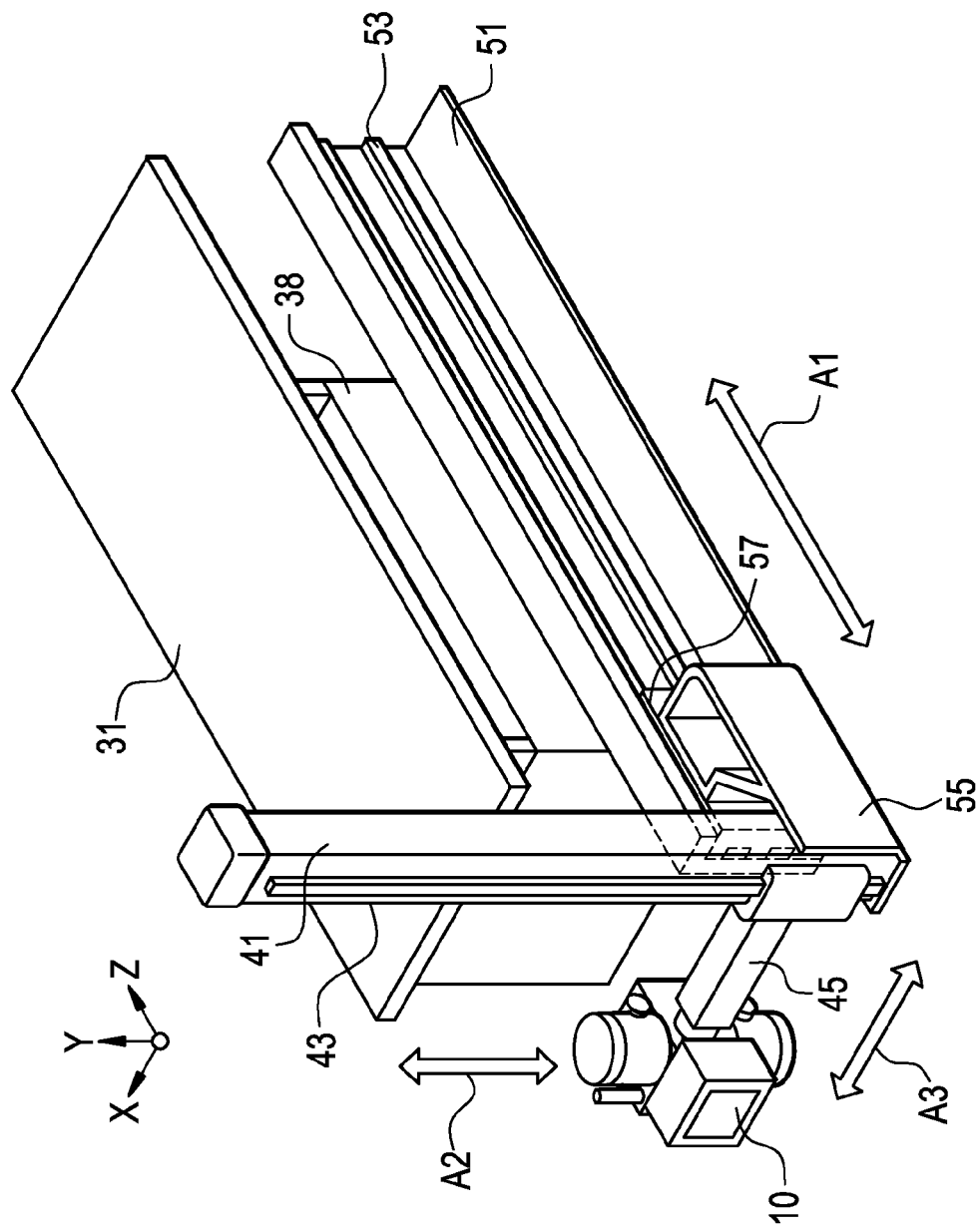
FIG. 3 is a back perspective view illustrating the constructions of the table 31 and the guide support post 41 employed in the embodiment.

Construction of moving device for X-ray tube unit. FIG. 2 is a front perspective view showing the constructions of the table 31 and the guide support post 41 employed in the embodiment. FIG. 3 is a back perspective view showing the constructions of the table 31 and the guide support post 41.

The table 31 is supported by a base or cradle 38. Some of the motor driver 89 or the like in the operation console 80 may be built in the cradle 38.

A rail support side wall 51 is provided on the back side of the cradle 38. At least one linear guide rail 53 is provided along the longitudinal direction of the table 31. A movable stage 57 is provided so as to be combined with the linear guide rail 53. The movable stage 57 is moved in the direction indicated by arrow A1 under the rotation of an unillustrated ball screw by the second drive motor 23 (see FIG. 1). When the second drive motor 23 is of a linear motor, the ball screw or the like becomes unnecessary.

An off center arm 55 is attached to the movable stage 57. The off center arm 55 has a structure which supports the guide support post 41. In FIG. 2, the off center arm 55 has such a form as to be protruded in an X direction (transverse direction of the table 31) from the rail support side wall 51 and protruded on the right side (Z direction: longitudinal direction of the table 31) from the right edge of the rail support side wall 51. That is, the off center arm 55 is formed in an L-shaped fashion as viewed from above.

The off center arm 55 takes such a form as to be protruded from the right edge of the rail support side wall 51 to the right side to enable an X-ray tube unit carrier 45 supporting the X-ray tube unit 10 to be lowered to the utmost limit of the floor. When the off center arm 55 simply extends from the right edge of the rail support side wall 51 to its left side, the X-ray tube unit carrier 45 collides with the rail support side wall 51 as the X-ray tube unit carrier 45 approaches the floor. Therefore, the X-ray tube unit 10 cannot be lowered to the floor.

Since the center of gravity of the off center arm 55 is placed in a position away from above the axial line of the linear guide rail 53, a load is imposed on the linear guide rail 53. Therefore, the off center arm 55 may preferably be made as light as possible. As is understandable from FIGS. 2 and 3, the off center arm 55 is held in a hollow structure and has such a structure that its strength and lightweight are made compatible. Incidentally, the off center arm 55 may take such a structure as to be combined directly with the linear guide rail 53 without providing the movable stage 57.

A tip portion of the off center arm 55 is coupled to its corresponding lower portion of the guide support post 41. The guide support post 41 takes on a hollow structure for the purpose of its lightweight. The guide support post 41 has one or two or more vertical linear guide rails 43 around the outer periphery of the guide support post 41. The X-ray tube unit carrier 45 is provided so as to be combined with the vertical linear guide rails 43. The X-ray tube unit carrier 45 is moved up and down along the vertical linear guide rails 43. An unillustrated ball screw is rotated by the first drive motor 21 (see FIG. 1) so that the X-ray tube unit carrier 45 is moved in the direction indicated by arrow A2. The ball screw or the like becomes unnecessary when the first drive motor 21 is of a linear motor. Bearings, which slide in contact with the floor, are disposed below the guide support post 41 to support the self weights of the guide support post 41 and X-ray tube unit 10.

The X-ray tube unit carrier 45 comprises a base portion 45-1 combined with the vertical linear guide rails 43 and an arm portion 45-2 that extends in the X direction. The X-ray tube unit 10 is supported by the arm portion 45-2. The X-ray tube unit 10 is provided in such a manner that the arm portion 45-2 thereof can be expanded and contracted and manually moved in the direction indicated by arrow A3. The expansion and contraction of the arm portion 45-2 may be position-controlled by a drive motor. The X-ray tube unit 10 is connected to the arm portion 45-2 by a ball joint structure and rotatable in a 360° direction with respect to an X axis. Further, the X-ray tube unit 10 is also rotatable even in a Y-axis or Z-axis direction. Therefore, the X-ray tube unit 10 is capable of applying an X-ray beam in an arbitrary direction according to the photographed region of the subject.

Figure 4A:
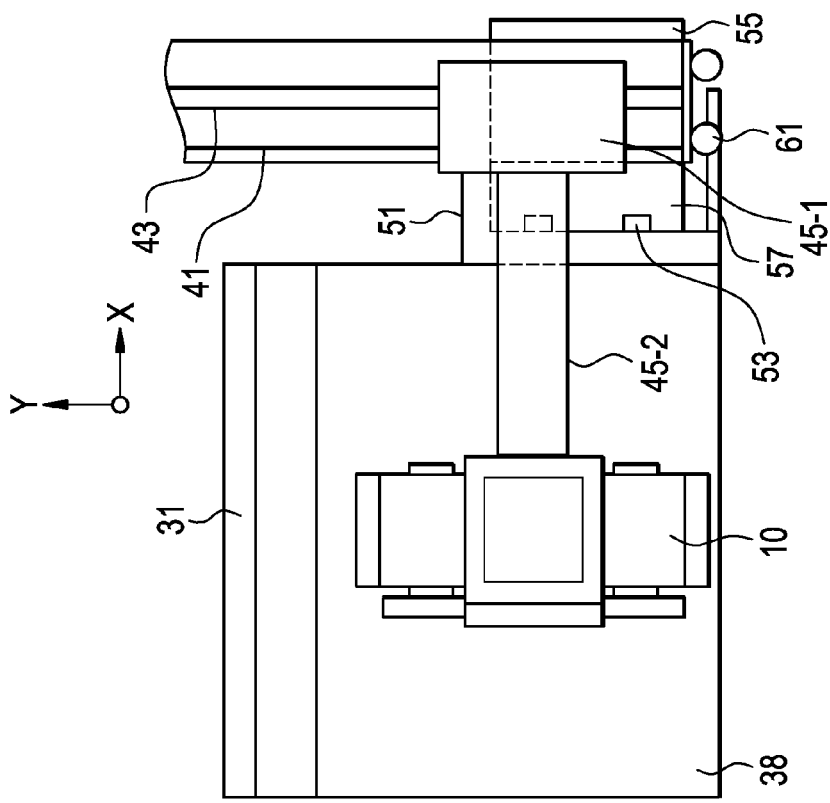
FIG. 4(a) is an enlarged front view depicting the constructions of the table 31 and the guide support post 41 in a state in which an X-ray tube unit 10 has been detached.
Figure 4B:
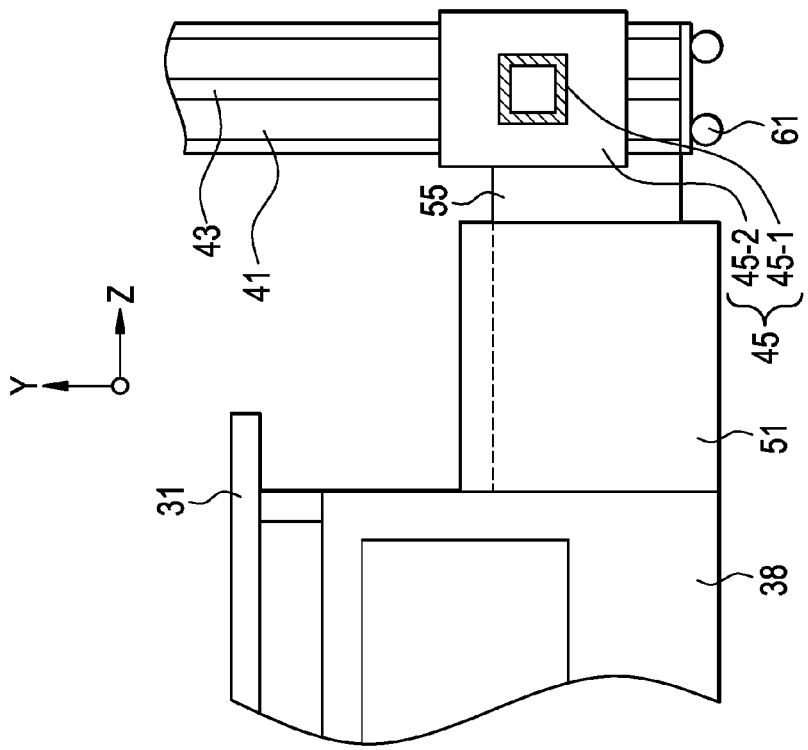
FIG. 4(b) is a side view thereof.

Support constructions of guide support post 41 and off center arm 55. FIGS. 4(a) and 4(b) are enlarged views showing support constructions of the off center arm 55 and the guide support post 41. FIG. 4(a) is an enlarged front view showing constructions of the table 31 and the guide support post 41, and FIG. 4(b) is a side view thereof. Incidentally, the X-ray tube unit 10 is in a detached state in FIG. 4(a) to make it easy to see the bearings 61 used as the sliding members.

In order to lower the X-ray tube unit 10 to as low a position as possible, the off center arm 55 is not disposed on the Y axis of the linear guide rail 53. Therefore, it is difficult to support the self weights of the X-ray tube unit 10, the guide support post 41 and the off center arm 55 in a cantilevered state. Accordingly, the guide support post 41 is provided with the bearings 61 corresponding to the sliding members at locations where they slide in contact with the floor of the guide support post 41. The bearings 61 are constructed so as to support the self weights of the X-ray tube unit 10, the guide support post 41 and the off center arm 55 and to be movable in the Z direction. When the off center arm 55 adopts such a structure that it supports all weights of the guide support post 41, the bearings 61 may be mounted to the off center arm 55.

FIG. 5(a) is a top view showing the constructions of the table 31 and the guide support post 41, and FIG. 5(b) is a front view thereof. FIG. 6 is a flowchart for the transfer of the X-ray tube unit 10. Since the X-ray tube unit 10 can be lowered to the floor unlike the conventional apparatus, the X-ray tube unit carrier 45 collides with the table 31 or the rail support side wall 51. In order to prevent this collision before happens, such an operation as to be described below is performed upon the transfer or traveling of the X-ray tube unit 10.

Figure 5:
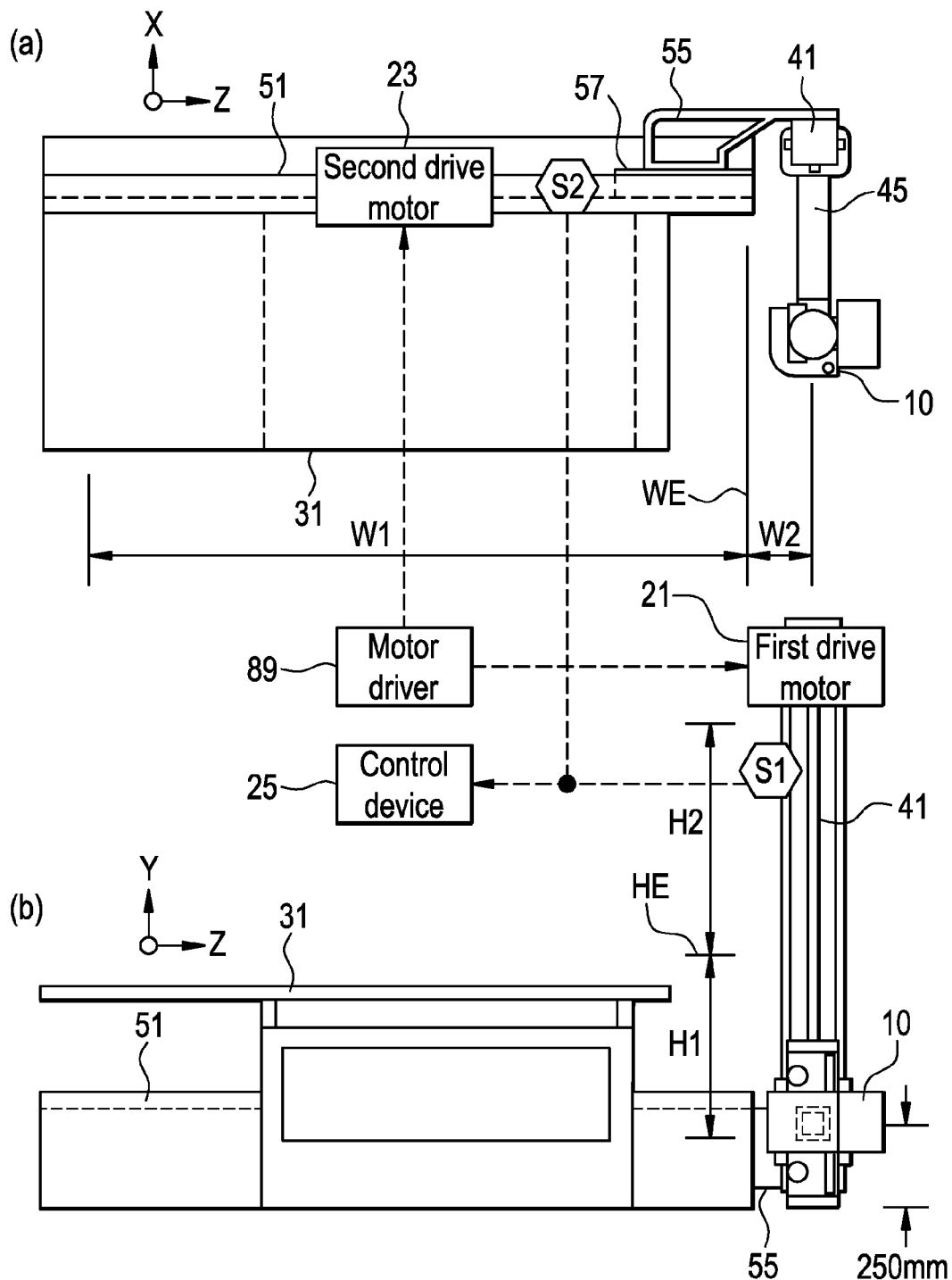
FIG. 5(a) is a top view showing the constructions of the table 31 and the guide support post 41.
FIG. 5(b) is a front view thereof.
Figure 6:
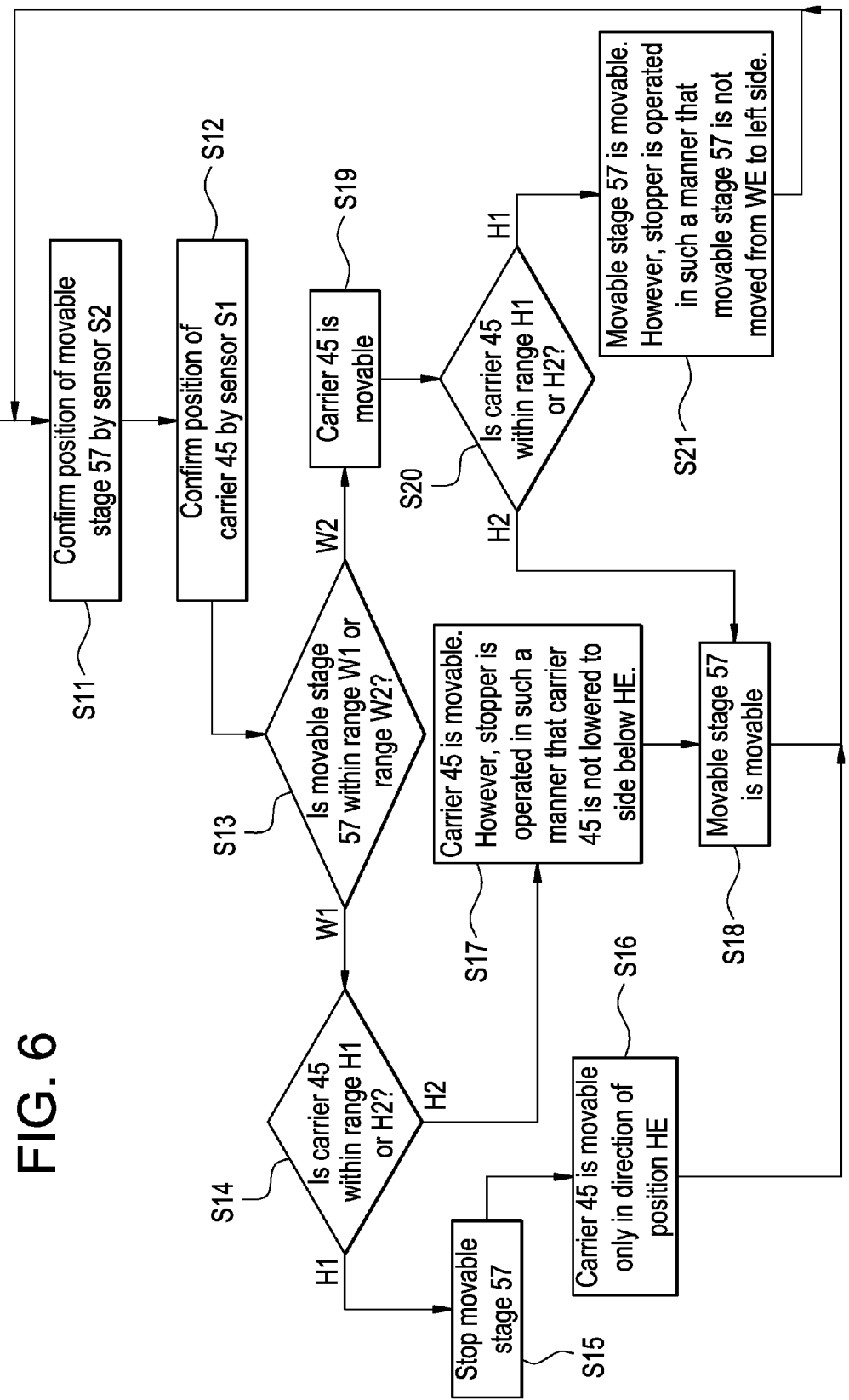
FIG. 6 is a flowchart for the transfer of the X-ray tube unit 10.
Figure 7:
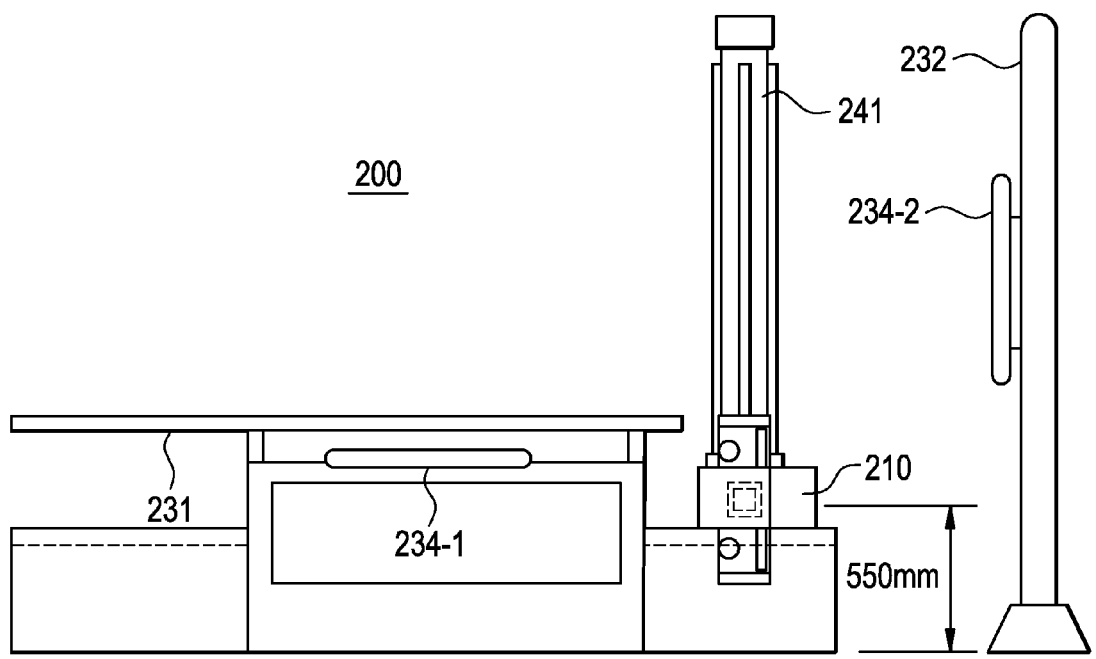
FIG. 7 shows a conventional X-ray radiography apparatus 200.

In FIG. 5, a position sensor S1 is disposed between the rail support side wall 51 and the movable stage 57. The position sensor S1 is provided so as to be capable of grasping or identifying the position of the movable stage 57. As shown in FIG. 5(a), the position sensor S1 may preferably identify whether the movable stage 57 is disposed in either a range W1 or a range W2.

A position sensor S2 is disposed between the guide support post 41 and the X-ray tube unit carrier 45. The position sensor S2 is provided so as to be capable of identifying the position of the X-ray tube unit carrier 45. As shown in FIG. 5(b), the position sensor S2 may preferably identify whether the X-ray tube unit carrier 45 is disposed in either a range H1 or a range H2.

A signal from the position sensor S1 or the position sensor S2 is sent to a control device 25. The control device 25 transmits a control signal to the motor driver 89, based on the signal, so that the motor driver 89 drives the first drive motor 21 and the second drive motor 23.

Control on the transfer of the X-ray tube unit 10 will be explained using a flowchart shown in FIG. 6.

At Step S11 of FIG. 6, the position sensor S2 confirms the position of the movable stage 57. A signal from the position sensor S2 is transmitted to the control device 25.

At Step S12, the position sensor S1 confirms the position of the X-ray tube unit carrier 45. A signal from the position sensor S1 is also transmitted to the control device 25.

At Step S13, the control device 25 determines whether the movable stage 57 is placed in either the range W1 or W2. If it is found that the movable stage 57 is placed in the range W1, then the control device 25 proceeds to Step S14. If it is found that the movable stage 57 is placed in the range W2, then the control device 25 proceeds to Step S19.

At Step S14, the control device 25 determines whether the X-ray tube unit carrier 45 is disposed in either the range H1 or H2. If it is found that the X-ray tube unit carrier 45 is placed in the range H1, then the control device 25 proceeds to Step S15. If it is found that the X-ray tube unit carrier 45 is placed in the range H2, then the control device 25 proceeds to Step S17.

At Step S15, the movable stage 57 stops. The second drive motor 23 may be supplied with a brake signal to stop the movable stage 57. Alternatively, the movable stage 57 may be provided with an electromagnetic stopper to make it unable for the movable stage 57 to move.

At Step S16, the control device 25 controls the X-ray tube unit carrier 45 such that it gets out of the range H1 because the X-ray tube unit carrier 45 is within the range H1 accidentally. That is, the X-ray tube unit carrier 45 can travel only in the direction of a position HE.

At Step S17, the X-ray tube unit carrier 45 is capable of moving within the range H2. However, the control device 25 controls the X-ray tube unit carrier 45 in such a manner that it does not enter the side below the position HE, i.e. it does not fall within the range H1. The guide support post 41 is provided with an electromagnetic stopper, which limits the traveling or transfer of the X-ray tube unit carrier 45 to the range H2.

At Step S18, the movable stage 57 is movable even within both of the range W1 and the range W2.

Next, when the movable stage 57 is placed in the range W2, the X-ray tube unit carrier 45 is movable even within both the ranges H1 and H2 at Step S19. The X-ray tube unit carrier 45 is movable to nearly the floor. Thus, the X-ray tube unit 10 can apply an X-ray beam to regions below the knees of the subject in a state in which the subject is standing.

At Step S20, the control device 25 determines whether the X-ray tube unit carrier 45 is disposed in either the range H1 or H2. If it is found that the X-ray tube unit carrier 45 is placed in the range H1, then the control device 25 proceeds to Step S21. If it is found that the X-ray tube unit carrier 45 is placed in the range H2, then the control device 25 proceeds to Step S18. When the control device 25 proceeds to Step S18, the movable stage 57 is movable even within both of the ranges W1 and W2 as mentioned above.

At Step S21, the movable stage 57 is movable within the range H2. In FIG. 5(a), however, a stopper is operated to prevent the movable stage 57 from being moved from a position WE to the left side. Thus, the X-ray tube unit carrier 45 is prevented from accidentally colliding with the rail support side wall 51 or the table 31.

Although the longitudinal direction is divided into the range W1 and the range W2 in FIG. 5 or 6, it may be divided into three or more according to the length of the table 31 or the length of the rail support side wall 51. The traveling or moving range of the X-ray tube unit carrier 45 may also be divided into three or more without being divided into the ranges H1 and H2.

Although the medical X-ray CR apparatus 100 has been described in the present embodiment, the present invention can be applied even to an industrial X-ray CR apparatus to enable X-ray radiography with respect to a target member from various angles.

The invention claimed is:

1. An X-ray radiography apparatus comprising:
   a table having a transverse direction and a longitudinal direction, said table comprising a first X-ray detector and configured to carry a subject thereon;
   an X-ray generator configured to apply X rays to the subject placed on said table; and
   an X-ray generator moving device configured to move said X-ray generator in the longitudinal direction of said table and in an upward direction and in a downward direction, said X-ray generator moving device comprising:
      a guide rail disposed in the longitudinal direction and facing a side direction in the neighborhood of said table;
      a guide support post configured to guide said X-ray generator in the upward direction and in the downward direction; and
      a movable stage configured to move along said guide rail, said movable stage extending in a transverse direction and coupled to said guide rail at a first end, said movable stage having a length that is greater than a width of said guide support post; and
      an off-center arm coupled at a first end to said movable stage and at a second end to said guide support post, said off-center arm extending in the longitudinal direction, said off-center arm having a length that enables said off-center arm to support said guide support post outside from an edge portion of said guide rail when said movable stage is moved to the edge portion of said guide rail.

2. The X-ray radiography apparatus according to claim 1, further comprising a stand comprising a second X-ray detector, said stand disposed adjacent to the subject.

3. The X-ray radiography apparatus according to claim 1, wherein said guide support post comprises a carrier configured to move said X-ray generator in the transverse direction.

4. The X-ray radiography apparatus according to claim 1, wherein said off-center arm is configured to slide in contact with a floor.

5. The X-ray radiography apparatus according to claim 2, wherein said off-center arm is configured to slide in contact with a floor.

6. The X-ray radiography apparatus according to claim 1, wherein said guide support post comprises a sliding member configured to slide in contact with a floor.

7. The X-ray radiography apparatus according to claim 2, wherein said guide support post comprises a sliding member configured to slide in contact with a floor.

8. The X-ray radiography apparatus according to claim 1, further comprising:
   a control device configured to control a transfer of said X-ray generator, such that when said movable stage is placed in a first range as viewed in the longitudinal direction, said control device controls said X-ray generator in such a manner that said X-ray generator is moveable in the upward direction and in the downward direction within a predetermined height range of said guide support post.

9. The X-ray radiography apparatus according to claim 2, further comprising:
   a control device configured to control a transfer of said X-ray generator, such that when said movable stage is placed in a first range as viewed in the longitudinal direction, said control device controls said X-ray generator in such a manner that said X-ray generator is moveable in the upward direction and in the downward direction within a predetermined height range of the said guide support post.

10. The X-ray radiography apparatus according to claim 1, further comprising:
    a control device configured to control a transfer of said X-ray generator, such that when said X-ray generator is placed at a predetermined height or less, said control device controls said movable stage in such that said movable stage is moved only within a second range.

11. The X-ray radiography apparatus according to claim 2, further comprising:
- a control device configured to control a transfer of said X-ray generator, such that when said X-ray generator is placed at a predetermined height or less, said control device controls said movable stage in such that said movable stage is moved only within a second range.

12. An X-ray generator moving device for use in an X-ray radiography apparatus that includes a table having a transverse direction and a longitudinal direction, the table capable of placing a subject thereon, and including a first X-ray detector and an X-ray generator configured to apply X-rays to the subject placed on the table, said X-ray generator moving device comprising:
- a guide rail disposed in the longitudinal direction and facing a side direction in the neighborhood of the table;
- a guide support post configured to guide the X-ray generator in the upward direction and in the downward direction;
- a movable stage configured to move along said guide rail, said movable stage extending in a transverse direction and coupled to said guide rail at a first end, said movable stage having a length that is greater than a width of said guide support post; and
- an off-center arm coupled at a first end to said movable stage and at a second end to said guide support post, said off-center arm extending in the longitudinal direction, said off-center arm having a length that enables said off-center arm to support said guide support post outside from an edge portion of said guide rail when said movable stage is moved to the edge portion of said guide rail, said X-ray generator moving device configured to move the X-ray generator in the longitudinal direction of the table and in the upward direction and in the downward direction.

13. The X-ray generator moving device according to claim 12, wherein said X-ray generator moving device further comprises a carrier positioned within said guide support post, said carrier configured to move the X-ray generator in the transverse direction.

14. The X-ray generator moving device according to claim 12, wherein said off-center arm is configured to slide in contact with a floor.

15. The X-ray generator moving device according to claim 12, wherein said guide support post comprises a sliding member configured to slide in contact with a floor.

16. The X-ray radiography apparatus according to claim 12, further comprising:
- a control device configured to control a transfer of the X-ray generator, such that when said movable stage is placed in a first range as viewed in the longitudinal direction, said control device controls the X-ray generator in such a manner that the X-ray generator is moveable in the upward direction and in the downward direction within a predetermined height range of said guide support post.

17. The X-ray radiography apparatus according to claim 12, further comprising:
- a control device configured to control a transfer of the X-ray generator, such that when the X-ray generator is placed at a predetermined height or less, said control device controls said movable stage in such that said movable stage is moved only within a second range.

18. The X-ray radiography apparatus according to claim 13, further comprising:
- a control device configured to control a transfer of the X-ray generator, such that when the X-ray generator is placed at a predetermined height or less, said control device controls said movable stage in such that said movable stage is moved only within a second range.

* * * * *